(12) United States Patent
Pitman et al.

(10) Patent No.: US 10,421,701 B2
(45) Date of Patent: Sep. 24, 2019

(54) METHOD FOR MATERIAL PACKAGING AND DEVELOPING ROTATIONALLY ANISOTROPIC MATERIALS

(71) Applicant: RAYTHEON COMPANY, Waltham, MA (US)

(72) Inventors: Michael C. Pitman, Tucson, AZ (US); Teresa J. Clement, Tucson, AZ (US); Glafkos K. Stratis, Tucson, AZ (US); Alphonso A. Samuel, Tucson, AZ (US); Alex Dely, Tucson, AZ (US); Wayne L. Sunne, Tucson, AZ (US)

(73) Assignee: RAYTHEON COMPANY, Waltham, MA (US)

( * ) Notice: Subject to any disclaimer, the term of this patent is extended or adjusted under 35 U.S.C. 154(b) by 101 days.

(21) Appl. No.: 15/425,141

(22) Filed: Feb. 6, 2017

(65) Prior Publication Data

US 2018/0222825 A1 Aug. 9, 2018

(51) Int. Cl.
| | |
|---|---|
| *C07C 13/62* | (2006.01) |
| *B82Y 15/00* | (2011.01) |
| *B82Y 30/00* | (2011.01) |
| *B82Y 25/00* | (2011.01) |
| *B82Y 10/00* | (2011.01) |

(Continued)

(52) U.S. Cl.
CPC .............. *C07C 13/62* (2013.01); *B82Y 10/00* (2013.01); *B82Y 15/00* (2013.01); *B82Y 20/00* (2013.01); *B82Y 25/00* (2013.01); *B82Y 30/00* (2013.01); *B82Y 40/00* (2013.01); *G02B 26/026* (2013.01); *H01G 9/20* (2013.01); *H01L 51/0052* (2013.01); *H01L 51/0098* (2013.01);

(Continued)

(58) Field of Classification Search
CPC . H01L 51/0052; H01L 51/0098; B82Y 10/00; B82Y 15/00; B82Y 20/00; B82Y 30/00; B82Y 25/00; B82Y 40/00; G11C 2213/14; G02B 26/026
See application file for complete search history.

(56) References Cited

U.S. PATENT DOCUMENTS

| | | |
|---|---|---|
| 3,911,038 A | 10/1975 | Maulding |
| 4,547,317 A | 10/1985 | Kamhi |

(Continued)

OTHER PUBLICATIONS

International Searching Authority; Notification of Transmittal of the International Search Report and the Written Opinion of the International Searching Authority, or the Declaration; dated Apr. 20, 2018; International Application No. PCT/US2018/016612; International Filing Date Feb. 2, 2018; 5 pages.

(Continued)

*Primary Examiner* — Scott R. Walshon
*Assistant Examiner* — Jasper Saberi
(74) *Attorney, Agent, or Firm* — Cantor Colburn LLP

(57) ABSTRACT

A support structure for a reconfigurable molecule includes a first support portion having a first mounting region; a second support portion having a second mounting region; and a rotatable molecule anchored between the first support portion and the second support portion on the first mounting region and the second mounting region, the rotatable molecule having an internal rotational axis extending from the first mounting region to the second mounting region; wherein the first support portion and the second support portion are mirror images of one another.

5 Claims, 8 Drawing Sheets

(51) Int. Cl.
  *G02B 26/02*  (2006.01)
  *B82Y 40/00*  (2011.01)
  *H01L 51/00*  (2006.01)
  *B82Y 20/00*  (2011.01)
  *H01G 9/20*  (2006.01)
  *H01L 51/05*  (2006.01)
  *C07C 15/28*  (2006.01)

(52) U.S. Cl.
  CPC .......... *H01L 51/0595* (2013.01); *C07C 15/28* (2013.01); *C07C 2603/54* (2017.05); *G11C 2213/14* (2013.01)

(56) References Cited

U.S. PATENT DOCUMENTS

| | | | | |
|---|---|---|---|---|
| 6,430,511 | B1* | 8/2002 | Tour | B82Y 10/00 |
| | | | | 435/6.11 |
| 2001/0033937 | A1* | 10/2001 | Michl | B82Y 10/00 |
| | | | | 428/447 |
| 2008/0002333 | A1* | 1/2008 | Vincent | H01G 7/023 |
| | | | | 361/502 |
| 2008/0269486 | A1* | 10/2008 | Zhou | B82Y 10/00 |
| | | | | 544/250 |
| 2008/0309864 | A1* | 12/2008 | Lee | C09K 19/32 |
| | | | | 349/139 |
| 2009/0286065 | A1* | 11/2009 | Bonifazi | B82B 3/00 |
| | | | | 428/315.5 |
| 2012/0128878 | A1* | 5/2012 | Li | B82Y 30/00 |
| | | | | 427/215 |

OTHER PUBLICATIONS

Written Opinion of the International Searching Authority; International Application No. PCT/US2018/016612; International Filing Date Feb. 2, 2018; Priority Date Feb. 6, 2017; 7 pages.

A. Andre et al., "Hybrid Quantum Information Processing with Polar Molecules," American Institute of Physics, 2006, pp. 128-135.

Stratis, et al. "Electric Field Dependence of the Competition Between Permanent and Induced Dipole Orientation in Suspensions of Large Anisotropic Particles," Electromagnetics, 1991, vol. 11, pp. 309-323.

\* cited by examiner

METHOD FOR MATERIAL PACKAGING AND DEVELOPING ROTATIONALLY ANISOTROPIC MATERIALS

BACKGROUND

The present invention relates to nanomaterials, and more specifically, to nanomaterials as support structures.

Generally, nanomaterials are materials composed of nanoscale unit cells. The individual unit cells may have sizes, at least in one dimension, between 1 and 1,000 nanometers (nm), or between 1 and 100 nm.

Nanomaterials may be natural or synthetic. Natural nanomaterials occur in nature. Biological systems can feature natural, functional nanomaterials, such as virus capsid walls and inorganic crystal growths. Examples of synthetic nanomaterials include, for example, graphene, carbon nanotubes, inorganic nanomaterials (e.g., quantum dots, nanowires and nanorods), and metal oxide nanowires. Other examples of nanoscale structures used in nanomaterials include porphyrins, cyclodextrins, and phtalocines.

Materials with structure at the nanoscale often have unique optical, electronic, or mechanical properties. Nanostructural chemistry is used to prepare materials with predetermined shapes and topography. Primary applications of self-assembling nanostructures are focused on, for example, nanowires, components of molecular scale electronics, and dye sensitive solar cells.

SUMMARY

According to an embodiment, a support structure for a reconfigurable molecule includes a first support portion having a first mounting region; a second support portion having a second mounting region; and a rotatable molecule anchored between the first support portion and the second support portion on the first mounting region and the second mounting region, the rotatable molecule having an internal rotational axis extending from the first mounting region to the second mounting region; wherein the first support portion and the second support portion are mirror images of one another.

According to another embodiment, a support structure for a reconfigurable molecule includes a first support portion having a first mounting region; a second support portion having a second mounting region; a rotatable nonpolar molecule anchored between the first support portion and the second support portion on the first mounting region and the second mounting region; a first rotational axis extending through the rotatable nonpolar molecule from the first mounting region to the second mounting region; and a second rotational axis extending through the rotatable nonpolar molecule, the second rotational axis being orthogonal or non-orthogonal to the first rotational axis.

Yet, according to another embodiment, a method of packaging a reconfigurable molecule in a solid state includes providing a support structure including a first support portion having a first mounting region and a second support portion having a second mounting region, the first support portion and the second support portion being mirror images of one another; and anchoring a rotatable molecule between the first support portion and the second support portion on the first mounting region and the second mounting region, the rotatable molecule having an internal rotational axis extending from the first mounting region to the second mounting region; wherein the support structure allows the rotatable molecule to rotate through the internal rotational axis upon application of an applied electric field.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

FIGS. 1-7B illustrate exemplary packaging (support structures) for solid state materials according to embodiments, in which:

FIG. 1 illustrates system components of a reconfigurable polar molecule packaged within a support structure;

FIG. 2 illustrates the tunable electromagnetic (EM) response of a solid state reconfigurable polar molecule packaged within a support structure;

FIG. 3 illustrates a packaged solid state material having individual molecules arranged in a lattice;

FIG. 6 illustrates a reaction scheme for bonding the primary rotating element in the packaging architecture;

FIG. 7B illustrates a packaging design with multiple axes for three-dimensional rotational anisotropy.

DETAILED DESCRIPTION

Because of their polar nature and rotational anisotropy, solid state polar molecules (the subject of embodiments of the invention described herein) may be used in a variety of RF and IR applications, thermal applications, quantum computing, spintronics, etc. One advantage of solid state polar molecules is that they have a wider thermal operating range compared to liquid polar molecules. Solid state polar molecules also have faster response times compared to liquid polar molecules. Furthermore, polar liquid molecules may be more sensitive to EM fields under certain circumstances or condition. For example, if the EM field is sufficiently strong, then translation and/or diffusion can occur, instead of rotation. Under some circumstances, due to their liquid state, liquid polar molecules may also become inherently disordered (or lose their alignment). Another challenge of liquid polar molecule materials is that they may operate at a limited range of temperatures due to the the molecules' dispersive and vibrational interactions with the host environment.

Accordingly, various embodiments described herein provide self-assembling building blocks that provide empty space as a solid matrix packaging for reconfigurable polar molecules. The solid matrix enables introduction of solid state primary materials that have internal degrees of freedom, while still maintaining insulation from a diffusive environment. Thus, the packaging structures preserve internal degrees of freedom for rotational motion, as well as govern assembly characteristics.

In some embodiments, the packaging scheme insulates rotatable polar molecules from temperature effects and minimizes diffusive interactions with the primary rotating material, while simultaneously exhibiting the intended shape and geometric properties to control self-assembly into the intended spatial arrangement. The packaging allows control of the specific orientation axis of the internal degree of freedom with respect to the crystallographic unit cell parameters, or with respect to externally applied electric fields. Further, the packaging introduces an adaptive and controllable anisotropy into the basic crystallographic unit system, which provides advantages in a variety of applications.

As used herein, the term "reconfigurable" when used in reference to a molecule means rotating in response to an applied external electric field.

As used herein, the term "polar" when used in reference to a molecule means having a net dipole as a result of partial negative and positive charges due to asymmetrically arranged polar bonds.

As used herein, the term "nonpolar" when used in reference to a molecule means having no net dipole due to equal sharing of electrons between two atoms of a diatomic molecule or symmetrical arrangement of polar bonds in a more complex molecule.

Figure 1:
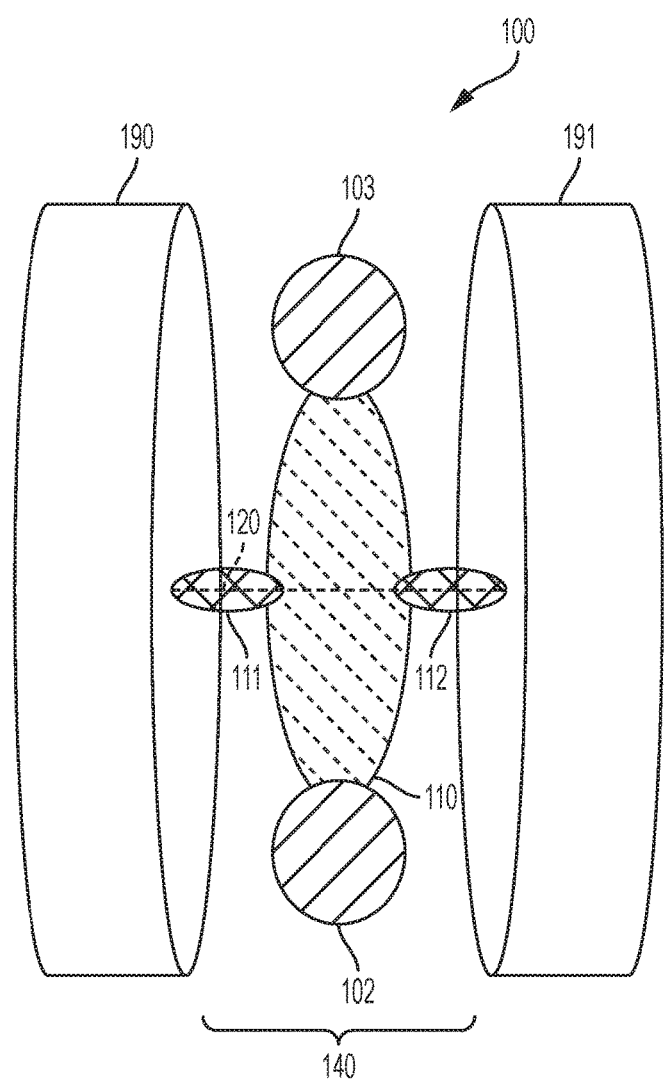

Turning now to the Figures, FIGS. 1-7B illustrate exemplary packaging (support structures) for solid state materials according to embodiments. FIG. 1 illustrates system components of a reconfigurable polar molecule 100 packaged within a support structure (first support 190 and second support 191) according to an embodiment. The primary rotating element 140 of the reconfigurable polar molecule 100 includes an elongated segment 110 having a first charged end 102 and a second charged end 103. Elongated segment 110 is substantially rigid, symmetric, and nonpolar. The elongated segment 110 provides a rigid scaffold that does not bend or twist. The elongated segment 110 has an elongated shape, or an elliptical shape, in some embodiments. The elongated segment 110 is defined by a long longitudinal axis and a shorter lateral axis.

First charged end 102 and second charged end 103 are each arranged on the longitudinal axis of elongated segment 110. First charged end 102 and second charged end 103 are arranged on opposing ends of elongated segment 110 and form a permanent dipole through the longitudinal axis. First charged end 102 is a permanent positive ionic charge, or cation. Second charged end 103 is a permanent negative ionic charge, or an anion. First charged end 102 and second charged end 103 are not induced dipoles. First charged end 102 and second charged end 103 are permanent ionic charges. First charged end 102 and second charged end 103 are permanent ionic charges that are opposite charges. In one example, first charged end 102 is a permanent positive charge, or cation, and second charged end 103 is a permanent negative charge, or anion. In another example, first charged end 102 is a permanent negative charge, and second charged end 103 is a permanent positive charge.

Although first charged end 102 and second charged end 103 are shown as being arranged on distal ends of elongated segment 110, first charged end 102 and second charged end 103 do not have to be specifically positioned on the far distal ends of elongated segment 110. In other words, the ionic charge of the first charged end 102 and second charged end 103 may be formed from a group that includes other atoms or groups such that the other atoms or groups are arranged on the distal ends. The rigid scaffold of elongated segment 110 ensure that first charged end 102 and second charged end 103 do not collapse onto one another.

As mentioned above, elongated segment 110 has an elliptical shape. Elongated segment 110 may include hydrocarbon systems with aromatic rings, planar fused rings, and/or planar heterocyclic molecules. Suitable hydrocarbon systems may include one or more aromatic rings (polyaromatic ring structures), one or more conjugated ring structures, one or more substituted aromatic rings, one or more saturated hydrocarbons, one or more unsaturated hydrocarbons, one or more substituted hydrocarbons, or any combination thereof. Elongated segment 110 may include substitutions on the hydrocarbon systems, provided that the substitutions result in a nonpolar molecule.

In one exemplary embodiment, elongated segment 110 is an anthracene derivative having the following structure (structure I):

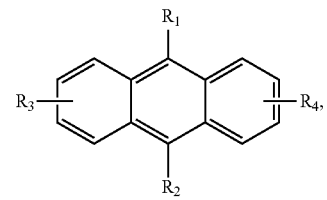

wherein $R_1$ and $R_2$ are each an ethynyl group; $R_3$ is a positively charged ionic group; and $R_4$ is a negatively charged ionic group.

Elongated segment 110 is not limited to organic hydrocarbon systems. In some embodiments, elongated segment 110 may include other nanoparticles, including, but not limited to, helices, carbon nanotubes, or combinations thereof. However, regardless of the composition, elongated segment 110 should remain substantially symmetric and nonpolar so that, as discussed below, primary rotating segment 140 may freely rotate.

Elongated segment 110 is derivatized at each end on the longitudinal axis to form first charged end 102 and second charged end 103. First charged end 102 and second charged end 103 may include any positively charged ionic group or any negatively charged ionic group. Non-limiting examples of positively charged ionic groups include positively charged amine groups, ammonium groups, phosphonium groups, sulfonium group, salts thereof, or any combination thereof. Non-limiting examples of negatively charged ionic groups include carboxylate groups, phosphate groups, phosphonate groups, sulfate groups, sulfonates groups, nitrate groups, nitrite groups, tosylate groups, brosylate groups, mesylate groups, selenate groups, salts thereof, or any combination thereof.

Elongated segment 110 is connected to a first support 190 by a first bridging group 111. Elongated segment 110 is connected to a second support 191 by a second bridging group 112. First bridging group 111 and second bridging group 112 are each connected to first support 190 and second support 191, respectively, by one or more interactions or bonds. First bridging group 111 and second bridging group 112 are arranged at opposing sides of elongated segment 110 on the shorter lateral axis of elongated segment 110 and along the axis of rotation 120. First bridging group 111 and second bridging group 112 are also arranged substantially perpendicular to the permanent dipole formed on the longitudinal axis of elongated segment 110. As described below, first bridging group 111 and second bridging group 112 allow free rotation of elongated segment 110 with respect to first support 104 and second support 105, respectively.

The interactions and/or bonds between first bridging group 111 and first support 190 and second bridging group 112 and second support 191 depend on the identities of the constituent groups. The interactions and/or bonds between first bridging group 111 and first support 1190 and second bridging group 112 and second support 191 include, for example, covalent bonds, hydrogen bonds, electrostatic interactions, hydrophobic interactions, metal complexation interactions, or any combination thereof.

First bridging group 111 and second bridging group 112 may be linear, nonpolar hydrocarbon groups. First bridging group 111 and second bridging group 112 may be the same or different. First bridging group 111 and second bridging group 112 anchor elongated segment 110 on axis of rotation 120 and provide a low barrier to free rotation (described below in FIG. 2). The axis of rotation 120 extends through the center of mass of primary rotating element 140. Each of first bridging group 111 and second bridging group 112 may be, for example, a linear hydrocarbon group, such as an alkynyl group, or an alkynyl-containing group. In one example, first bridging group 111 and second bridging group are each linear ethynyl groups or linear cyano groups. First bridging group 111 and second bridging group 112 may form carbon-carbon covalent bonds with first support 190 and second support 191, respectively.

Elongated segment 110 can freely rotate under the influence of an external stimulus of appropriate magnitude and orientation, as described in further detail below with reference to FIG. 2. For example, under the influence of an externally applied electric field, elongated segment 110 rotates along the axis of rotation 120. The permanent dipole of elongated segment 110 is directed approximately perpendicular to first bridging group 111 and approximately perpendicular to second bridging group 112.

First support 190 and second support 191 form attachment points for the primary rotating element 140 and serve as the packaging material that houses the rotatable polar molecules in the solid state. First support 190 and second support 191 may be any nonpolar support structures or moieties. First support 190 and second support 191 each have mounting regions (first mounting region and second mounting region, respectively) upon which the first bridging group 111 and second bridging group 112 will bond, for example, via a covalent bond and/or other interaction or bonds. As a result, the rotatable molecule will be anchored between the first mounting region and the second mounting region, with the internal rotational axis extending there between. In some embodiments, the first support 190 and second support 191 are mirror images of one another.

First support 190 and second support 191 should provide an unobstructed path for rotation about the axis of rotation 120. First support 190 and second support 191 thus provide the material housing (packaging) around the rotational path (axis of rotation 120) of primary rotating element 140, which allows for full rotation in response to applied electric fields. The material housing forming first support 190 and second support 191 may be the same or different. The material housing forming first support 191 and second support 191 insulates primary rotating element 140 from dispersion and ambient vibrational modes. The packaging protects the primary rotating element 140 and prevents other molecules from interacting with or diffusing the spinning dipole. The shape and chemical make-up of the packaging forming first support 190 and second support 191 governs three-dimensional (3D) assembly into solid state 3D materials.

The materials and composition of the first support 190 and second support 191 may generally vary and depend on the desired properties of the solid state material and particular application. The first support 190 and second support 191 each include nonpolar molecules. The size and shape of each of the first support 190 and second support 191 may generally vary and depend on the type of solid state material desired, as such properties govern the three-dimensional assembly into the solid state material.

The first support 190 and second support 191 provide insulating walls that are optimized for symmetric, three-dimensional assembly. First support 190 and second support 191 are thus symmetric. First support 190 and second support 191 are each also optimized for temperature stability, rotational axis stability, and electro-optic (EO) properties for the particular application window.

In one embodiment, the first support 190 and second support 191 may include a low-k dielectric material. For example, first support 190 and second support 191 materials may have a dielectric constant, or k-value, in a range from about 2 to about 8. In one embodiment, first support 190 and second support 191 include polyaromatic ring structure-containing walls that minimize dispersion, which are described in further detail below.

In an exemplary embodiment, solid state reconfigurable polar molecule 100 has the following structure (structure II):

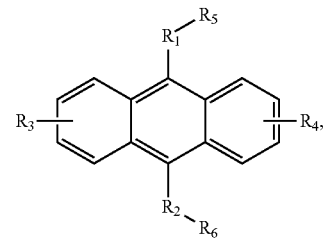

wherein $R_1$ and $R_2$ are each independently a $C_2$-$C_4$ alkyl group, a $C_2$-$C_4$ alkenyl group, a $C_2$-$C_4$ alkynyl group, a cyano group, or any combination thereof; $R_3$ is a positively charged ionic group; $R_4$ is a negatively charged ionic group; and $R_5$ and $R_6$ are each independently an non-polar support moiety. The $C_2$-$C_4$ alkyl group, $C_2$-$C_4$ alkenyl group, and $C_2$-$C_4$ alkynyl group may be branched, unbranched, substituted, or unsubstituted.

In another embodiment, solid state reconfigurable polar molecule 100 has the following structure (structure III):

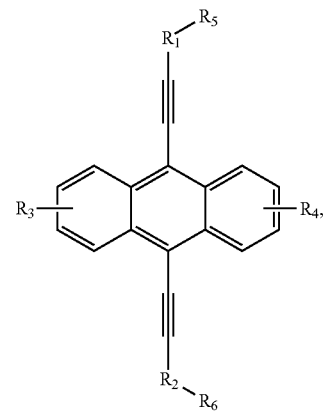

wherein $R_1$ and $R_2$ are each independently a single bond, a $C_2$-$C_4$ alkyl group, a $C_2$-$C_4$ alkenyl group, a $C_2$-$C_4$ alkynyl group, a cyano group, or any combination thereof; $R_3$ is a positively charged ionic group; $R_4$ is a negatively charged ionic group; and $R_5$ and $R_6$ are each independently an non-polar support moiety. The $C_2$-$C_4$ alkyl group, $C_2$-$C_4$ alkenyl group, and $C_2$-$C_4$ alkynyl group may be branched, unbranched, substituted, or unsubstituted.

When solid state reconfigurable polar molecule 100 includes an alkynyl group, as shown in structure III above, the axis of rotation 120 (shown in FIG. 1) extends through the alkynyl group and is arranged substantially perpendicular to the permanent dipole formed on elongated segment 110 from first charged end 102 and second charged end 103 on the long longitudinal axis.

Figure 2:
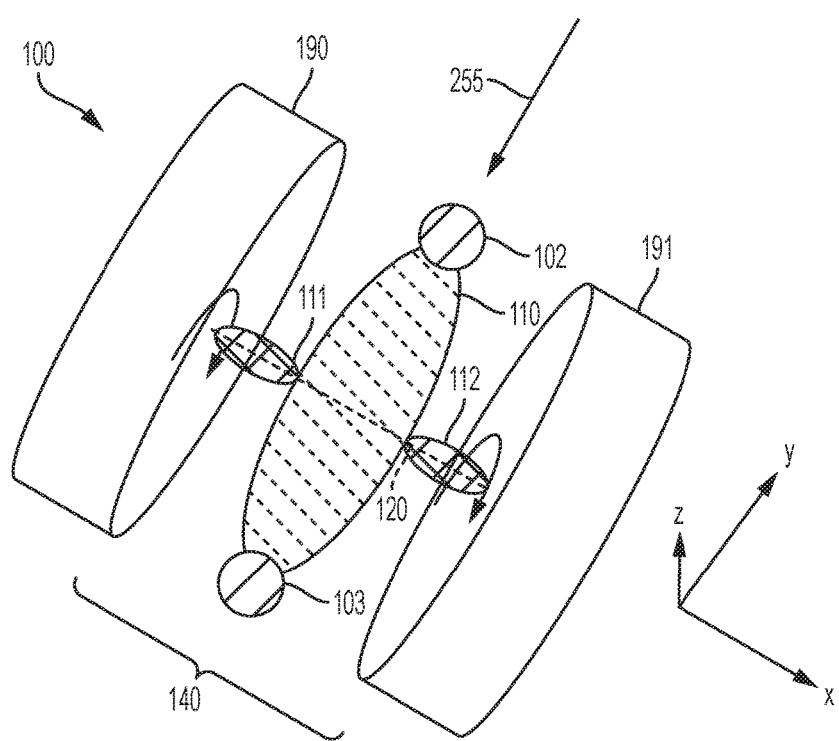

FIG. 2 illustrates the tunable electromagnetic response of the reconfigurable polar molecule 100 packaged within a support structure. In the coordinate system shown, primary rotating element 140 lies in the x-y plane between first support 190 and second support 191, and the z-axis points into the page. The axis of rotation 120 is located along the x-axis.

Upon application of an external electric field 255, primary rotating element 140 rotates along its axis of rotation 120, away from the x-y plane and into the z-plane by a rotation angle θ. Although the electric field 255 is shown as being applied in the y-axis direction, the electric field 255 may be applied in any direction(s). The magnitude of the applied electric field 255 determines the amount of rotation and the rotation angle θ. The permanent dipole across the elongated segment 110 due to the first charged end 102 and second charged end 103 induces the rotation. Because primary rotating element 140 is rigid, it remains anchored in first support 190 and second support 191 during rotation. Also because first bridging group 111 and second bridging group 112 are linear groups, they allow free rotation towards the z-plane, which is arranged substantially perpendicular to the x-y plane.

As the primary rotating element 140 rotates through rotation angle θ, a number of stable and unstable conformations may be possible. Some conformations may be more energetically favored than others. The stability of the conformations depends on the composition of the primary rotating element 140 and the surrounding packaging 304 (including first support 190 and second support 191). Upon application of the electric field 255, primary rotating element 140 rotates through rotation angle θ to the lowest energy conformation.

The above-described reconfigurable polar molecules may be combined into a plurality and ordered or arranged in a lattice to form a solid state material. Compared to liquid crystalline materials, the solid state materials have improved thermal stability and therefore may be used in wider temperature ranges. For example, the reconfigurable polar molecules and solid state materials made therefrom may be used at temperatures in a range from about a cryogenic temperature to about 400° C.

The reconfigurable polar molecules described above also provide other advantages. The molecules can be used as a dopant for a host material. For example, if polar molecules are in a dielectric material, under certain conditions, they may be aligned and become radiators (antenna/dipoles). In another example, the polar molecule's adaptive orientation will impact the reflectivity/transmissivity of the material. Furthermore, using them as dopants in certain applications can decrease the energy gap in certain dielectrics.

The polar molecules and materials may be used in RF and IR optical applications. The polar molecules and materials also can be applied in the fields of spintronic devices and logic gates and quantum optics. These polar molecules also can interact with incoming signals of various polarizations, functioning as a sensor. Further, the molecules and materials may be used as a polarization transformer. Because of their size, the molecules can be used to implement switching capability down to the nanometer scale.

The shape of the support structure/packaging (first support 190 and second support 191) governs three-dimensional assembly of the reconfigurable polar molecule 100 into the lattice of the solid state material.

Figure 3:
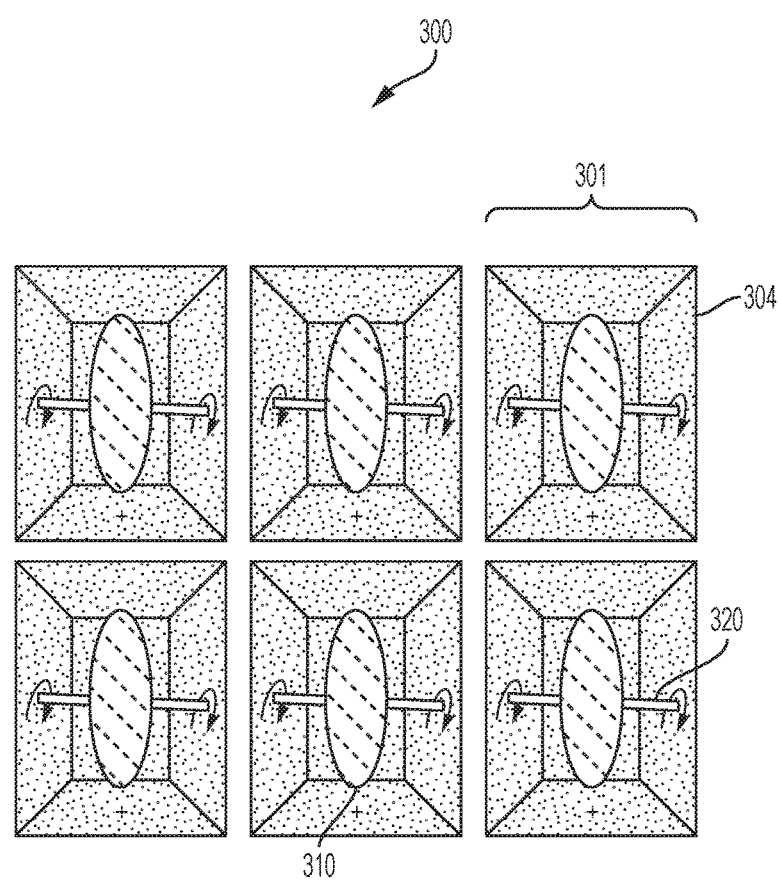

In an exemplary embodiment, FIG. 3 illustrates a packaged solid state material 300 having unit cells 301 of reconfigurable polar molecules arranged in a lattice. Each of the unit cells 301 includes a primary rotating element that includes an elongated segment that includes a first charged end with a positive charge and a second charged end with a negative charge. The primary rotating element is a rigid molecule with a permanent dipole. The primary rotating element has an axis of rotation 320 that extends through its center of mass. The primary rotating element is anchored by bridging groups (first bridging group and second bridging group) (not shown in FIG. 3 for clarity) in a packaging 304 (including a first support and second support). The packaging 304 provides a housing around the rotational path of the primary rotating element to insulate from dispersion and ambient vibrational modes.

Figures 4A, 4B:
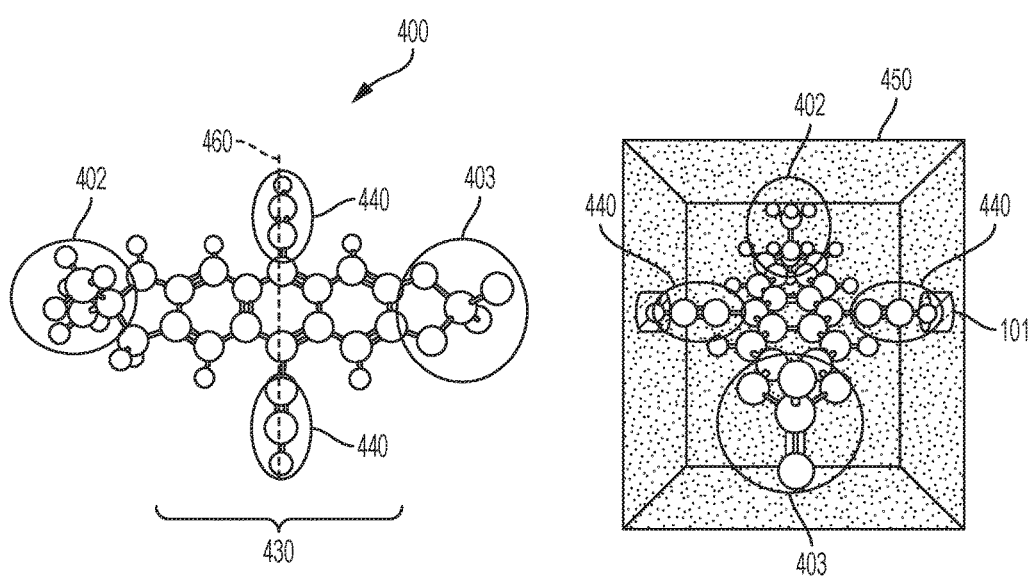
FIG. 4A is a three-dimensional illustration of a primary rotating element of a reconfigurable polar molecule.
FIG. 4B is a primary rotating element anchored within a packaging architecture.

FIG. 4A is a three-dimensional illustration of a primary rotating element 400 according to an embodiment. The primary rotating element 400 is an ammonium phosphate ethynyl-anthracene derivative, which has the following chemical structure (structure IV):

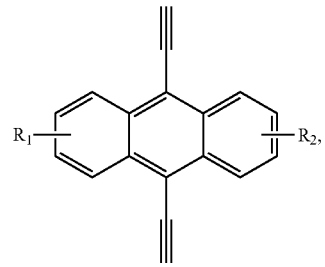

wherein $R_1$ is an ammonium group (—$N(R)_3^+$), and $R_2$ is a phosphate group ($PO_4(R)_2^-$).

An ethynyl-anthracene molecule forms elongated segment 430. The ethynl groups arranged on opposing sides of the central ring portion of the anthracene form the bridging groups 440 (first bridging group and second bridging group) that will anchor the primary rotating element 400 to the packaging 450, as shown in FIG. 4B. The axis of rotation 460 extends through the bridging groups 440.

The ethynyl-anthracene molecule is derivatized with a positively charged ammonium group to form first charged end 402. The ethynyl-anthracene derivative is derivatized with a negatively charged phosphate group to form second charged end 403. However, the derivatives on the ethynyl-anthracene molecule portion may be optimized for specific applications.

FIG. 4B is a primary rotating element 400 anchored within a packaging 450 architecture. The packaging 450 (or support) include polyaromatic walls, in some embodiments, that minimize dispersion during rotation of the primary rotating element 400. The ammonium group and the phosphate group provide a permanent dipole across the primary rotating element 400, which is oriented through an applied electric field. The ethynyl groups forming the bridging groups 440 that anchor the primary rotating element 400 on the axis of rotation 460 that provides a low barrier to rotation.

It is noted that FIG. 4B is shown for illustrative purposes only. Although the ethynyl groups of primary rotating element 430 are shown as being superimposed into packaging 450, the ethynyl groups will form covalent bonds (carbon-carbon bonds) with the molecule of the packaging 450. For example, the reaction between the primary rotating element 400 and packaging 450 is illustrated by the following reaction scheme (reaction scheme I):

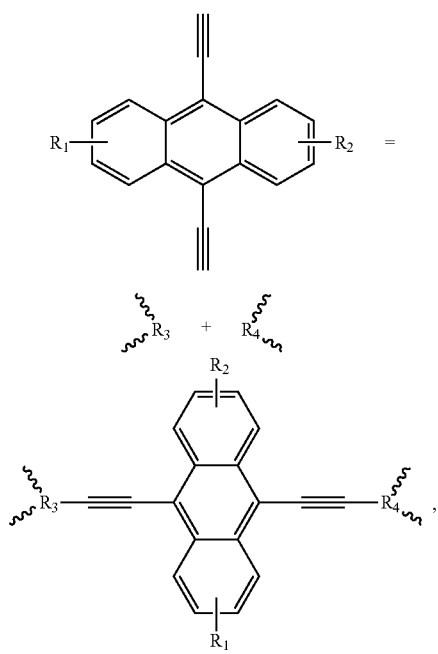

wherein $R_1$ is an ammonium group, $R_2$ is a phosphate group, $R_3$ is a carbon-containing group of a first support, $R_4$ is a carbon-containing group of a second support, and covalent carbon-carbon bonds are formed between the ethynyl groups and each of $R_3$ and $R_4$.

The reconfigurable polar molecules described in the above embodiments may be used in a variety of applications, for example, as sensors or molecular switches. When used as a switch, the molecules are switched between "on" and "off" states. The reconfigurable polar molecule may be placed between two electrodes so that an electric field with an appropriate magnitude and orientation, produced between the two electrodes, causes the primary rotating element to rotate. The orientation of the molecule located between the two electrodes can vary depending on the type of molecule selected and how the molecule is used.

When the reconfigurable polar molecules, and solid state materials made therefrom, are used as a sensor, the molecules can interact with incoming signals (electric fields) of various polarizations combined with local voltages for control purposes. For instance, by controlling the rotational anisotropy of the polar molecule, the reflectivity of the surface can be controlled, and therefore, the Radar Cross Section (RCS) can be controlled.

Figure 5A:
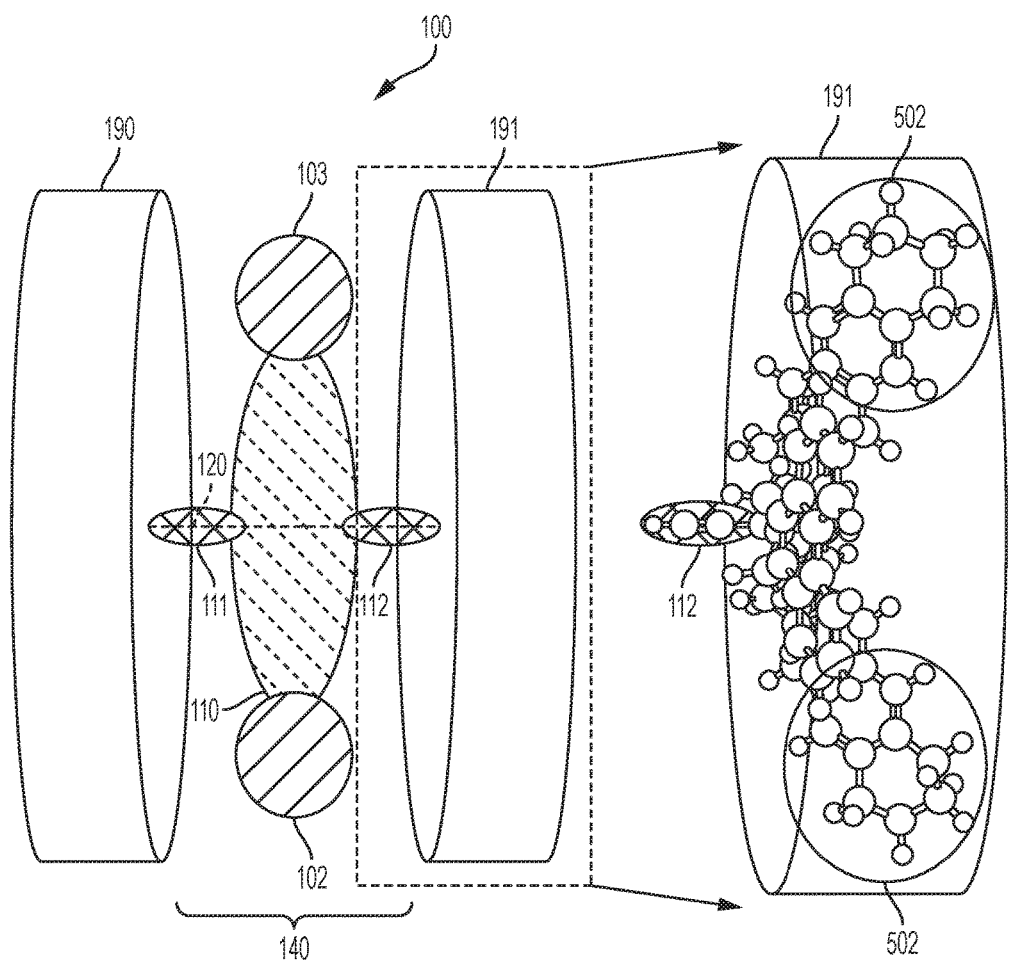
FIG. 5A is a three-dimensional illustration of an exemplary packaging architecture.

FIG. 5A is a three-dimensional illustration of an exemplary packaging architecture for primary rotating element 140 packaged within a support structure (first support 190 and second support 191), which is described above in FIG. 1. The wall construction forming the packaging of second support 191 is a mixed-saturation polyaromatic system.

Figure 5B:
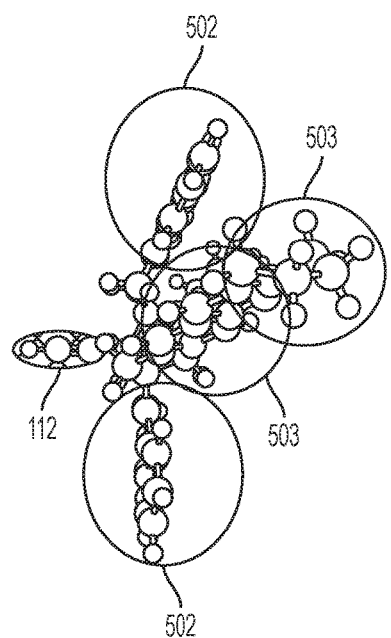
FIG. 5B is a side view of the three-dimensional illustration of FIG. 5A.

Second support 191 includes two sets of ring structures 502, as well as two sets of alkyl groups 503, as shown in FIG. 5B, which is a side view of molecule shown in FIG. 5A. The groups 503 also can be cyclo-alkyl groups, with varying degrees of unsaturation.

First support 190 and second support 191 insulate primary rotating element 140 and protect it from dispersive interactions. First support 190 and second support 191 also provide specific binding sites for the primary rotating element 140, or in particular, for the first bridging group 111 and second bridging group 112. First support 190 and second support 191 should each provide a binding site that will easily bond with first bridging group 111 and second bridging group 112. Because of the molecular and chemical nature of the molecules forming first support 190 and second support 191, the primary rotating element 140 is protected from interactions with the packaging.

Each set of ring structures 502 includes broken conjugation. In other words, each set of ring structures includes both aromatic rings and nonaromatic rings (or saturated rings) (i.e., an aromatic ring is fused with a nonaromatic ring). The fused organic ring structure of the molecule forming second support 191 breaks the extended conjugation. The resulting limited conjugation improves optical transparency. Extended conjugation generally results in visible color or other optical properties. However, limited conjugation, in contrast, does not impose additional optical properties to the primary polar molecular that it contains. As shown, the molecule is a low dielectric, nonpolar compound that is nonreactive with the primary rotating element 140. Although not shown, first support 190 may include the same molecule shown in the exemplary packaging architecture for second support 191.

Figure 5C:
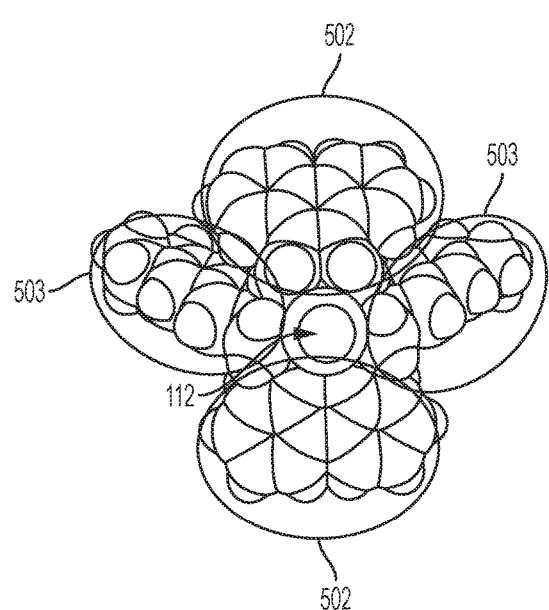
FIG. 5C is a space-filling view of the exemplary packaging architecture of FIGS. 5A and 5B.

FIG. 5C is a space-filling view of the exemplary packaging architecture of FIGS. 5A and 5B. The second bridging group 112 formed from the ethynyl group is shown in the central region of the molecule, with the ring structures 502 and alkyl groups 503 extending away from the central second bridging group 112. As shown, the packaging architecture exhibits internal mirror symmetry and may be a meso compound in some embodiments.

In addition to the structure shown in FIGS. 5A-5C, the first support 190 and second support 191 may include other molecules with both fused ring structures and/or alkyl groups. The alkyl groups may be branched and/or bulky groups. Including bulky groups along the rotational axis where the primary rotating element is mounted in the packaging reduces the reactivity of the primary rotating element with the packaging. To promote self-assembly, the rotatable molecule should be non-reactive with the first support 190 and second support 191, other than the intended mounting regions on the molecules. In other words, molecules forming first support 190 and second support 191 should have one biding site for a bridging group of the primary rotating element, with other portions of the molecule being nonreactive.

In one exemplary embodiment, each of first support 190 and second support 191 has the following structure (structure V):

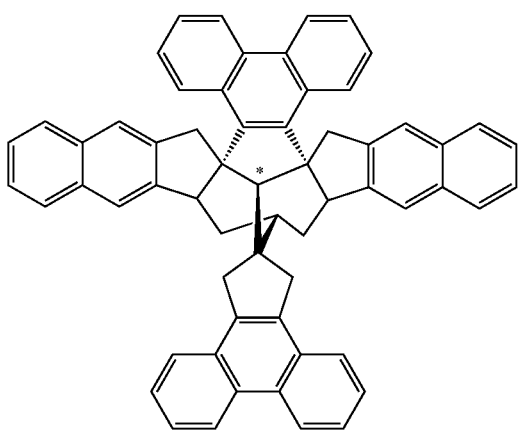

wherein each ring structure is optionally substituted, and the first bridging group 111 or second bridging group 112 bonds at the asterisk (*) position.

In one example, a first ethynyl group from primary rotating element covalently bonds to the asterisk (*) position of one molecule of structure V, and a second ethynyl group from primary rotating element covalently bonds to the asterisk (*) position of another molecule of structure V.

Figure 6:
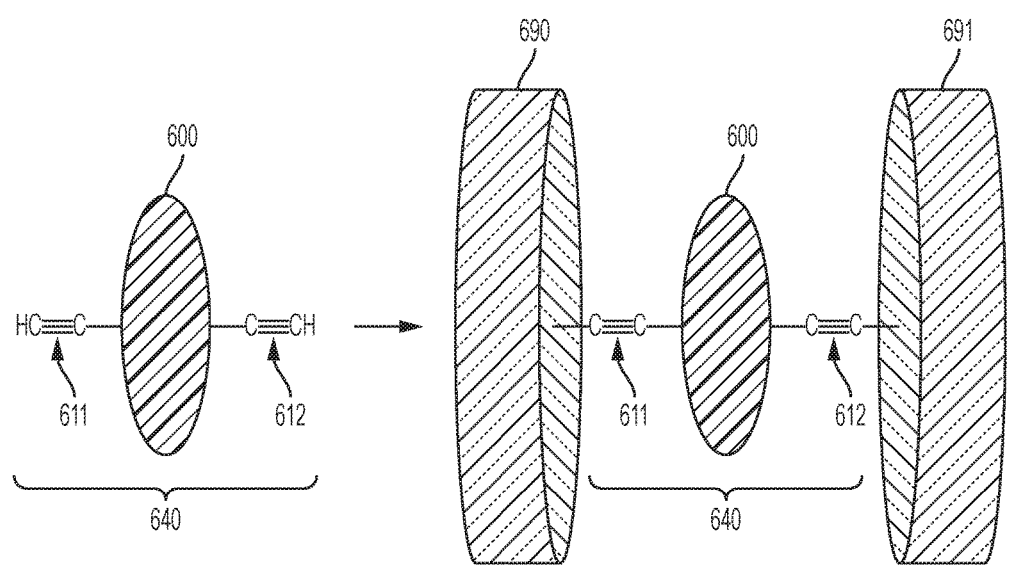

FIG. 6 illustrates a reaction scheme for bonding the primary rotating element 640 in the packaging architecture. Primary rotating element 640 includes reconfigurable polar molecule, a first bridging group 611, and a second bridging group 612. First bridging group 611 and second bridging group 612 each include an ethyne group. Primary rotating element 640 covalently bonds to first support 690 via the ethyne group of first bridging group 611 and second support 691 via the ethyne group of second bridging group 612. The covalent bonds between the ethyne groups and first support 690 and second support 691 are carbon-carbon bonds. Although additional bonds and/or interactions may stabilize the molecule.

In addition to the above-described molecules and structures, the packaging architectures may include other types of self-assembling structures. Non-limiting examples of suitable structures include carbon nanotubes, graphene, metal oxide nanowires, porphyrins, cyclodestrins, phtalocines, and pillared clays.

Pillared clays are two-dimensional microporous materials with a high surface area and permanent porosity. Pillared clays can be controllably hydrated to open clay layers and form "pillars" between the clay layers, which creates a high pore volume. Other molecules, such as lipids, can also be inserted between the clay layers to adjust the spacing. When a pillared clay is used as the packaging material, the rotating polar molecule can be grown or inserted in the pillars such that the molecule is embedded in the pillared clay. Thus, the rotating polar molecule can be embedded in the pillared clay such that the resulting structure has controllable anisotropy. Multiple layers of pillared clays may be used to create multiple rotational axes, as described below.

Figure 7A:
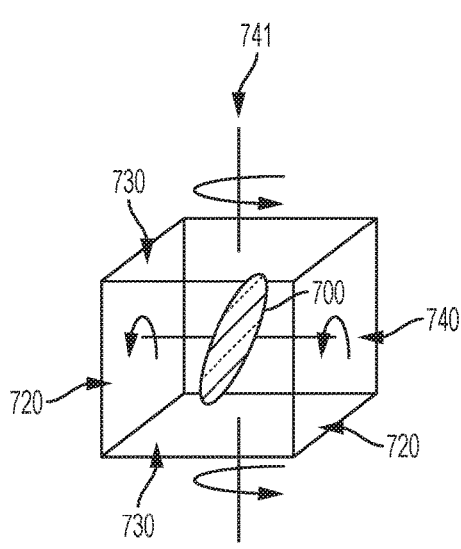
FIG. 7A illustrates a packaging design with multiple axes for three-dimensional rotational anisotropy.
Figure 7B:
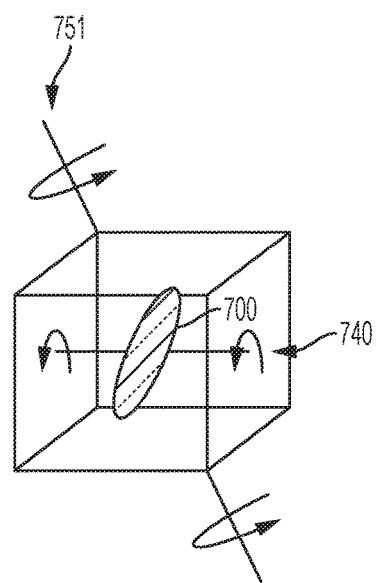

FIGS. 7A and 7B illustrate packaging designs with multiple axes for three-dimensional rotational anisotropy. In FIG. 7A, reconfigurable polar molecule 700 is arranged within a packaging scheme with two orthogonal rotational axes. Reconfigurable polar molecule 700 has an internal rotational axis and is arranged between supports as shown in, for example, FIG. 6. Another layer of packaging (or support) structures also surround reconfigurable polar molecule 700, which provides an additional orthogonal rotational axis 741. FIG. 7B illustrates a packaging scheme with two non-orthogonal rotational axes (internal rotational axis 740 and non-orthogonal rotational axis 751).

Although two rotational axes are illustrated in FIGS. 7A and 7B, the packaging scheme can provide any number of rotational axes, both orthogonal and non-orthogonal. The number and type of rotational axes depend on the type and number of packaging material layers. For example, multiple, orthogonal and non-orthogonal degrees of freedom can be accomplished by coupling packaging at different scales such that one layer is contained within another layer. The second (outer layer) packaging can mount the first (inner layer) packaging on an orthogonal or non-orthogonal axis, for example, as shown in FIGS. 7A and 7B, respectively. Multiple layers of packaging thus set the orientation of the internal degree(s) of freedom.

The above-described packaging schemes may be used in a variety of applications. The schemes allow implementation of controllable rotational anisotropy in areas, such as, Radar Cross Section (RCS) applications (e.g., polarimetric transformers), electronic devices (e.g., spintronics), optical devices (e.g., switches), reconfigurable structures, cyber technology applications, and quantum cryptography/computing.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A support structure for a reconfigurable molecule, comprising:
    a solid state matrix packaging comprising a first support portion having a first mounting region and a second support portion having a second mounting region;
    a rotatable nonpolar molecule in a solid state anchored between the first support portion and the second support portion on the first mounting region and the second mounting region;
    a first rotational axis extending through the rotatable nonpolar molecule from the first mounting region to the second mounting region; and
    a second rotational axis extending through the rotatable nonpolar molecule, the second rotational axis being orthogonal or non-orthogonal to the first rotational axis;
    wherein the support structure further comprises a layer of support structures arranged on the support structure to provide the second rotational axis.

2. The support structure of claim 1, wherein the first support portion and the second support portion are mirror images of one another.

3. The support structure of claim 1, wherein each of the first support portion and the second support portion is a meso-compound.

4. The support structure of claim 1, wherein the first support portion and the second support portion comprise pillared clays.

5. A solid state material comprising a plurality of the support structures of claim 1, wherein the plurality of the support structures are ordered in a lattice.

\* \* \* \* \*